United States Patent
Goeboeloes et al.

(10) Patent No.: US 7,214,829 B2
(45) Date of Patent: May 8, 2007

(54) METHOD FOR THE PRODUCTION OF PRIMARY AMINES BY HYDROGENATING NITRILES

(75) Inventors: Sandor Goeboeloes, Budapest (HU); Andras Fasi, Dunaujvaros (HU); Jozsef Margitfalvi, Budapest (HU); Laszlone Millian, Budapest (HU)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 147 days.

(21) Appl. No.: 10/505,638

(22) PCT Filed: Feb. 13, 2003

(86) PCT No.: PCT/EP03/01407

§ 371 (c)(1),
(2), (4) Date: Mar. 11, 2005

(87) PCT Pub. No.: WO03/070688

PCT Pub. Date: Aug. 28, 2003

(65) Prior Publication Data

US 2005/0159624 A1    Jul. 21, 2005

(30) Foreign Application Priority Data

Feb. 23, 2002  (DE)  ............... 102 07 926

(51) Int. Cl.
*C07C 209/48* (2006.01)
*B01J 25/00* (2006.01)
*B01J 25/02* (2006.01)

(52) U.S. Cl. ............ 564/493; 564/492; 502/301; 502/527.12

(58) Field of Classification Search .......... None
See application file for complete search history.

(56) References Cited

U.S. PATENT DOCUMENTS

| | | | |
|---|---|---|---|
| 2,165,515 A | 7/1939 | Schmidt | |
| 3,544,485 A | 12/1970 | Kuroda et al. | |
| 3,574,754 A | 4/1971 | Specken | |
| 3,891,707 A * | 6/1975 | Waddan | ........ 564/492 |
| 3,980,720 A | 9/1976 | Mabuchi et al. | |
| 4,207,263 A | 6/1980 | Hoffmann et al. | |
| 4,739,120 A | 4/1988 | Zuckerman | |
| 4,876,362 A | 10/1989 | Raddisson et al. | |
| 5,254,736 A | 10/1993 | Forquy | |
| 5,498,796 A | 3/1996 | Deckers et al. | |
| 5,777,166 A | 7/1998 | Cordier et al. | |
| 5,869,653 A | 2/1999 | Johnson | |
| 5,874,625 A | 2/1999 | Elsasser | |

FOREIGN PATENT DOCUMENTS

| | | |
|---|---|---|
| CN | 1242 260 | 1/2000 |
| GB | 1585480 | 3/1981 |
| JP | 6032 767 | 2/1994 |

OTHER PUBLICATIONS

Database CAPLUS on STN, Acc. No. 1964:59236, Ohta et al., Nippon Kagaku Kaishi (1921-47) (1953), Ind. Chem. Sect. 56, p. 330-2 (abstract).*
Database CAPLUS on STN, Acc. No. 1988:598152, Shimizu et al., Nippon Kagaku Kaishi (1988), 6, p. 881-5 (abstract).*
T. A. Johnson, et al., "Lithium Hydrodide Modified Sponge Catalysts for Control of Primary Amine Selectivity in Nitrile Hydrogenations", Proceedings of 18th Conf on Catalysis of Organic Reaction, Ed. by M.E. Ford, 2000, pp. 201-227.
M. Kalina et al., "Different Catalytic Properties of Nickel and Cobalt in the Reaction of Amines", Translated from Kinetika i Kataliz, vol. 10, No. 3, pp. 574-580, May-Jun. 1968.
E.J. Schwoegler et al., "Preparation of Certain Amines", Journal of Am. Chem Soc., vol. 61, pp. 3499-3502, Dec. 1939.
M. Besson et al., "Structure and Catalytic Properties in Hydrogenation of Valeronitrile of Raney Nickel Prepared from Cr and Mo Doped Ni2Al3 Alloys", Heterogeneous Catalysis and fine chemicalsII, ed M. Guisnet et al. Elsevier, 1991, pp. 113-120.
D.Djaouadi, et al., "Hydrogenation of Aliphatic Nitriles on Raney Nickel", Catalysis of Organic Reaction, ed. by Scaros et al., Marcel Dekker, pp. 423-429, 1995.
S. Xie et al., "Selective Hydrogenation of Stearonitrile Over Ni-B/ SiO2 Amorphous Catalysts in Comparison with Other Ni-based Catalysts", Applied Catalysis, vol. 189 (1999) pp. 45-52, Elsevier.
S. Sakakibra, J. Chem Soc., Japan Ind. Chem Sect, 56, pp. 497-499(1953).

* cited by examiner

*Primary Examiner*—Brian Davis
(74) *Attorney, Agent, or Firm*—Richard P. Silverman

(57) ABSTRACT

The present invention relates to an improvement in a process for preparing primary amines by hydrogenating nitriles. The improvement in the hydrogenation process is that a hydrogenation catalyst modified ex situ with preadsorbed alkali metal carbonate or hydrogencarbonate such as $K_2CO_3$ or $KHCO_3$ is used.

13 Claims, No Drawings

METHOD FOR THE PRODUCTION OF PRIMARY AMINES BY HYDROGENATING NITRILES

This application is a 371 of PCT/EP03/01407 filed.

The present invention relates to the preparation of primary amines by catalytically hydrogenating nitrites.

Hydrogenation of nitrites to produce amines is of great industrial importance owing to the wide-ranging applications of amines, such as the organic solvents, agrochemicals, pharmaceuticals, surfactants, and especially, the intermediate of nylon-6,6. The hydrogenation is usually carried out over Raney nickel catalyst in the liquid phase at elevated temperatures and hydrogen pressures, in which the ammonia is present to enhance the yield of the primary amine by inhibiting the formation of the secondary and tertiary amines.

Representative patents and articles illustrating the hydrogenation of nitrites to produce primary amines are as follows:

E. J. Schwoegler and H. Adkins, J. Am. Chem. Soc. 61, 3499 (1939) predicted and then demonstrated that adding sufficient ammonia to the hydrogenation of a nitrile would strongly inhibit the formation of secondary amine and thus greatly improve the selectivity to primary amine.

U.S. Pat. No. 2,165,515 discloses a process for the production of primary amines by the catalytic hydrogenation of nitrites using cobalt and cobalt promoted with barium or manganese.

S. Sakakibara et al., J. Chem. Soc. Japan, Ind. Chem. Sect., 56, 497 (1953) describe a method for preparing primary amines such as dodecylamine by the hydrogenation of nitrites such as lauronitrile with ammonia using Raney nickel catalyst.

U.S. Pat. No. 3,574,754 discloses a process for preparing primary amines by the hydrogenation of nitriles with ammonia using Raney nickel catalyst.

U.S. No. 4,739,120 discloses a process for the hydrogenation of nitrites to primary amine using a rhodium catalyst. The reaction is carried out in the presence of a two-phase solvent system comprising an aqueous phase and a water-immiscible organic phase.

M. Besson et al., Stud. Surf. Sci. Catal., Vol. 59, "Heterogeneous Catalystis and Fine Chemicals II", ed. M. Guisnet et al., 1991, pp. 113–120, reported a method for the production of primary amines from nitrites in the presence of cyclohexane, utilizing a Raney nickel catalyst doped with molybdenum or chromium.

EP Pat. No. 0,547,505 discloses a process for the production of dodecylamine by the catalytic hydrogenation of lauronitrile in the presence of ammonia using magnesium-nickel catalyst coprecipitated on a support.

Pol. Pat. No. 51,530 employed nickel catalyst to hydrogenate aliphatic nitrites and especially lauronitrile. Ammonia was present to suppress the production of secondary amine.

JP Pat. No. 7,941,804 discloses a process for producing primary amines by hydrogenating the nitrile in lower alcohol and cyclic hydrocarbon mixtures in the presence of alkali or alkali earth metal hydroxides and chromium modified Raney nickel catalyst.

JP Pat. No. 6,032,767 discloses a process for the hydrogenation of nitrites to primary amine using a Raney nickel catalyst in the presence of ammonia.

D. Djaouadi et al., Catal. Org. Reactions, 423 (1995) prepared a chromium and iron doped Raney nickel catalyst by alkali leaching of intermetallic alloys, $Ni_{40}Al_{60}$ or $Ni_{25}Al_{75}$ being the parent alloys. The selective hydrogenation of valeronitrile to the corresponding primary amine was performed in cyclohexane using a stirred autoclave. The improvement in selectivity to the primary amine with doping is mainly explained by a decrease of the rate of hydrogenation of the intermediate secondary imine, thus favoring reverse reactions.

S. Xie et al., Appl. Catal. A: General, 189, 45 (1999) reported the ammonia additive could greatly improve its selectivity to primary amine in the selective hydrogenation of stearonitrile over Ni—B/$SiO_2$ amorphous catalysts, although a slight decrease in the activity was observed. The amorphous structure of the catalyst and the alloying boron played key roles in promoting the hydrogenation activity and the selectivity to primary amines. However, no significant promoting effect of $KNO_3$ doped $SiO_2$ was observed.

Alkali metal hydroxide additives are also used to improve the selectivity in the hydrogenation of organic nitrites to amines. T. A. Johnson et al., Proceedings of the "18th Conference on Catalysis of Organic Reactions" ed. M. E. Ford, 2000, paper 13, reported that the selective hydrogenation of nitrile could be carried out using lithium hydroxide modified sponge nickel and cobalt catalysts.

U.S. Pat. No. 5,874,625 discloses a process for the catalytic hydrogenation of organic nitrites to primary amines using a slurry of Raney nickel catalyst and aqueous alkali metal hydroxide, wherein the Raney nickel catalyst and aqueous alkali metal hydroxide contribute from about 0.1 to about 3% water. The autoclave charge is pressurized with hydrogen, and then heated to a final temperature of about 110° C.

U.S. Pat. No. 5,777,166 discloses a process for the hydrogenation of nitriles to amines. The process comprises: a) doping a Raney nickel type catalyst with at least one additional metal element selected from Group IVb of the Periodic Classification of the Elements which is derived from an Ni/Al/doping element metallurgic precursor alloy and wherein the doping element/Ni ratio by weight is between 0.05 and 10%; and b) exposing the catalyst to a nitrile in a liquid reaction medium which dissolves the nitrile along with at least one inorganic base selected from the group consisting of LiOH, NaOH, KOH, RbOH, and CsOH and thereby hydrogenate the nitrile.

U.S. Pat. No. 5,869,653 discloses a process for the catalytic hydrogenation of nitrites which comprises contacting the nitrile with hydrogen in the presence of a sponge cobalt catalyst under ammonia-free conditions for effecting conversion of the nitrile group to the primary amine, the improvement in the hydrogenation process which resides in effecting the hydrogenation in the presence of a sponge cobalt catalyst treated with a catalytic amount of lithium hydroxide and effecting the reaction in the presence of water.

WO-01/66511 discloses a process for hydrogenating nitriles to amines, although no modification of the hydrogenation catalyst takes place before the hydrogenation.

Alkali metal carbonates were also used for promoting the selectivity of Raney nickel catalysts for the preparation of amines in the alkylation of ammonia or alkylamines with alcohols. French Pat. No. 2,351,088, Ger. Offen. No. 2,621, 449, Ger. Offen. No. 2,625,196 and Ger. Offen. No. 2,639, 648 disclose the preparation of tertiary amines by alkylation of secondary amines by alcohols with water removal in the liquid phase in the presence of hydrogenation-dehydrogenation catalyst such as Raney nickel or Raney cobalt and one or more basic alkali metal or alkali earth metal compounds. Thus a mixture of 774 kg n-dodecanol, 500 kg ethylbenzene, 10 kg $Na_2CO_3$, and 300 kg Raney nickel was heated to 130–5° C., hydrogen and dimethylamine were fed into the mixture with azeotroping of water until the theoretical amount of $H_2O$ was removed, and the catalyst was filtered off and the filtrate distilled to give 80% $RNMe_2$, 15% $R_2NMe$, and 5% $R_3N$ (R=n-dodecyl).

Ger. Offen. No. 2,645,712 discloses a process for the preparation of secondary amines by alkylation of ammonia by alcohols in the presence of hydrogenation-dehydrogenation catalyst and a basic alkali or alkali earth metal compound. Thus ammonia was fed at atmospheric pressure into a dephlegmator reactor containing stearyl alcohol, Raney nickel, and $Na_2CO_3$ at 90–140° C. with continuous removal of $H_2O$ to give >95% distearylamine.

Kalina, M. and Pashek, Yu. (Kinetika i Kataliz, 10, 574, 1969) reported on the use of $Na_2CO_3$ modified metallic cobalt and nickel catalysts for the liquid phase hydrogenation of palmitic nitrile. The addition of sodium carbonate to the reaction mixture at $Na_2CO_3$/catalyst/nitrile 5/5/100 weight ratio, 150° C. and 50 bar hydrogen pressure resulted in a decrease of secondary amine selectivity. The selectivity of the secondary amine measured at 50% conversion on Co, Ni, Co+$Na_2CO_3$, Ni+$Na_2CO_3$ catalysts was 17.4, 20.1, 11.0 and 12.2%, respectively.

A catalyst system containing supported nickel and alkaline carbonate was used for the preparation of dissymmetric aliphatic secondary alkylamines.

U.S. Pat. No. 5,254,736 and EP Pat. No. 0 526 318 disclose a process for the preparation of secondary methylalkyl amines of general formula: R—NH—$CH_3$, in which R is $C_{10}$–$C_{22}$ aliphatic chain, by amination reaction between an alcohol and a monoalkylamine. The amination reaction was carried out with a supported nickel catalyst in the presence of an alkali carbonate, potassium carbonate being the best, the weight ratio between the potassium carbonate and the nickel catalyst being between 1:4 and 1:1, under a hydrogen pressure between 10 and 50 bar. In a typical example 422 g dodecylamine (2.3 moles), 1460 g methanol (45 moles), 38.6 g supported nickel catalyst (Harshaw Ni 1404T), and 57.1 g $K_2CO_3$ were autoclaved at 180° C., 40 bar hydrogen pressure and 1800 rpm for 6 hours. The composition of the reaction product was 0% $RNH_2$, 85.9% RNHMe, 1.3% $RNMe_2$, 6.0% $R_2NH$, and 6.8% ROH, whereas on the unmodified catalyst the concentrations were 15.0%, 17.2%, 44.9%, 13.8%, and 9.1 %, respectively (R=n-dodecyl, Me=methyl).

The drawbacks to the previous processes disclosed in the patent literature for the preparation of primary amines by the hydrogenation of nitrites are as follows:
(i) Ammonia has to be used to decrease the selectivity of secondary and tertiary amines.
(ii) Despite the improved selectivity to primary amine achieved by the addition of an alkali metal hydroxide or carbonate, the controlled and reproducible interaction between the additive and the catalyst cannot be guaranteed.
(iii) As far as the alkali metal compound additive is used in comparable amount to the catalyst the presence of certain quantity of water in the reaction mixture is required. This makes the reuse of catalyst and the separation of reaction products more difficult.

Drawbacks (ii) and (iii) are also related to the process for the production of secondary amine from an alcohol and a primary amine over a supported nickel catalyst and in the presence of large amount of alkali metal carbonate added to the reaction mixture (U.S. Pat. No. 5,254,736 and EP Pat. No. 0 526 318).

The goal of this invention is to overcome the above drawbacks related to previous processes disclosed for the preparation of primary amines by the catalytic hydrogenation of nitrites. Thus the goal is to suppress the secondary and tertiary amine formation in the hydrogenation of nitrites to primary amines. The invention also aims at omitting ammonia or keeping its partial pressure as low as possible in the nitrile hydrogenation process.

It has been found that, surprisingly, in the hydrogenation of nitrites, for example fatty acid nitrites such as lauronitrile, in the absence of ammonia, alkali metal carbonate or hydrogencarbonate, especially $K_2CO_3$, is the best modifier of the hydrogenation catalyst for suppressing the selectivity for the secondary amine to at most 2%. The low selectivity for the secondary amine is maintained using an alkali metal carbonate or hydrogencarbonate up to a nitrile conversion of 99%. The modification of the hydrogenation catalyst using the alkali metal carbonate or hydrogencarbonate, such as $K_2CO_3$ or $KHCO_3$, may be carried out in a slurry using distilled water as the solvent.

The present invention thus provides a process for preparing a primary amine by hydrogenating nitrites, in which a reaction mixture which comprises
(a) at least one nitrile,
(b) hydrogen,
(c) optionally ammonia and
(d) at least one cobalt or nickel catalyst modified ex situ by adsorption of an alkali metal carbonate or alkali metal hydrogencarbonate is converted.

The invention further provides a modified cobalt or nickel catalyst obtainable by adsorption of an alkali metal carbonate or alkali metal hydrogencarbonate on a customary cobalt or nickel catalyst. Particular preference is given to Raney nickel catalysts.

The modification of the catalyst is effected using alkali metal carbonate or hydrogencarbonate. Useful alkali metals are Na, K, Rb, Cs. Preference is given to the alkali metal carbonates, and also in particular $K_2CO_3$ or $KHCO_3$. The adsorption is effected from a solution of the alkali metal carbonates or hydrogencarbonates having concentrations of preferably from 10 g/l up to 400 g/l. Preference is given to adsorption from aqueous solution, especially aqueous solution having concentrations of from 50 to 200 g/l.

Here, ex situ means that the catalyst has been modified outside, especially before, the hydrogenation reaction of nitrile to give amine which is catalyzed by it.

The weight ratio of dry catalyst to the solution of alkali metal carbonate or hydrogencarbonate is preferably from 50 to 350 g/l.

The untreated catalyst is preferably cobalt, nickel, Raney cobalt or Raney nickel. The catalysts may be used without or with promoters. Promoters are, for example, Fe, Mo, Cr, Ti, Zr. The catalysts may be applied to support materials. Such support materials are, for example, $SiO_2$, $Al_2O_3$, $ZrO_2$, MgO, MnO, ZnO, $Cr_2O_3$.

Particularly preferred embodiments are
Raney nickel without promoters, or with the promoters Fe, Mo, Cr, Ti, Zr
nickel on the support materials $SiO_2$, $Al_2O_3$, $ZrO_2$, MgO, MnO, ZnO, $Cr_2O_3$,
Raney cobalt without promoters, or with the promoters Ni, Cr
cobalt on the support materials $SiO_2$, $Al_2O_3$, MgO, MnO.

The untreated catalyst is preferably slurried in the solution of alkali metal carbonate or hydrogencarbonate and stirred under hydrogen or an inert gas, for example nitrogen, for from about 1 to 16 hours.

The excess of the solution is removed after the adsorption by filtration under inert gas, preferably nitrogen atmosphere. It is advantageous to wash the catalyst obtained after the adsorption with alcohol and then with a hydrocarbon.

In a preferred embodiment, the modified catalyst is obtained from the slurry by decanting and subsequently washing the catalyst three times with ethanol and twice with cyclohexane.

The alkali metal carbonate or hydrogencarbonates is present in the modified catalyst preferably in an amount of from about 2 to 12% by weight. In a particularly preferred embodiment, the modified catalyst contains $K_2CO_3$ or $KHCO_3$ in an amount of from about 6 to 7% by weight.

The process according to the invention is suitable for hydrogenating any nitriles. The nitrites are preferably of the formula R—CN where R is a saturated or unsaturated hydrocarbon group of from 1 to 32, preferably from 4 to 24, in particular from 8 to 22, carbon atoms. R is also preferably an alkyl group, in particular linear alkyl group. The modified catalyst is generally present in the reaction mixture in an amount of from 1 to 10% by weight based on the nitrile.

The reaction mixture may also contain a solvent. Suitable for this purpose are preferably short-chain alcohols, especially methanol, ethanol and propanol, and also hydrocarbons such as hexane, cyclohexane and toluene. The solvent may be present in the mixture in amounts of from 0 to 90% by weight, based on the reaction mixture.

When ammonia is added to the reaction mixture, the amount of ammonia in the reaction mixture should be from 1 to 10% by weight, based on the nitrile.

The nitrile hydrogenation over the modified catalyst is preferably carried out under a hydrogen pressure of from 1 to 200 bar, in particular from 2 to 30 bar.

The nitrile hydrogenation over the modified catalyst is preferably carried out in the temperature range from 60 to 250° C., in particular from 100 to 150° C.

EXAMPLES

Catalyst Modification

The catalysts of Examples 1 to 14 are Raney nickel catalysts.

Example 1

2 g potassium carbonate were dissolved in 20 ml distilled water (concentration, c=100 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The potassium content of the catalyst was 2.4% by weight.

Example 2

3 g potassium carbonate were dissolved in 20 ml distilled water (c=150 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The potassium content of the catalyst was 3.2% by weight.

Example 3

4 g potassium carbonate were dissolved in 20 ml distilled water (c=200 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The potassium content of the catalyst was 4.1 % by weight.

Example 4

8 g potassium carbonate were dissolved in 20 ml distilled water (c=400 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The potassium content of the catalyst was 4.6% by weight.

Example 5

3 g potassium carbonate were dissolved in 20 ml distilled water (c=150 g/l) and the 1.4 g wet (1 g dry) catalyst were suspended in the solution and stirred at room temperature for 1 hour. After modification the suspension was decanted. The potassium content of the catalyst was 7.1 % by weight.

Example 6

3 g potassium carbonate were dissolved in 20 ml distilled water (c=150 g/l) and the 1.4 g wet (1 g dry) catalyst were suspended in the solution and stirred at room temperature for 1 hour. After modification the suspension was filtered off under a nitrogen atmosphere. The potassium content of the catalyst was 3.2% by weight.

Example 7

3 g potassium carbonate were dissolved in 20 ml distilled water (c=150 g/l) and the 1.4 g wet (1 g dry) catalyst were suspended in the solution and stirred at room temperature for 16 hours under a nitrogen atmosphere. After modification the suspension was decanted and the catalyst was washed three times with 20 ml ethanol and twice with 20 ml cyclohexane. The potassium content of the catalyst was 3.3% by weight.

Example 8

1.3 g potassium carbonate were dissolved in 5 ml distilled water (c=150 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The potassium content of the catalyst was 3.1 % by weight.

Example 9

4 kg potassium carbonate were dissolved in 28 l distilled water (c=143 g/l) and the 2 kg wet (1.4 kg dry) catalyst were suspended in the solution and stirred at room temperature under a nitrogen atmosphere for 2 hours. After 20 hours the catalyst settled down and the excess of potassium carbonate solution was removed by vacuum. The catalyst was stored under a thin layer of potassium carbonate solution. Prior to use the suspension was decanted and the catalyst was washed three times with 20 ml ethanol and twice with 20 ml cyclohexane. The potassium content of the catalyst was 3.8% by weight.

Example 10

140 g potassium carbonate were dissolved in 610 ml distilled water (c=229 g/l alkali metal carbonate solution) and the 300 g wet (210 g dry) catalyst were suspended in the solution and stirred at room temperature under a nitrogen atmosphere for 2 hours. After modification the catalyst settled down overnight and the excess of solution was removed by vacuum. The modified Raney nickel catalyst was filtered off under nitrogen. The potassium content of the catalyst was 3.9% by weight.

Example 11

3 g potassium hydrogencarbonate were dissolved in 20 ml distilled water (c=150 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The potassium content of the catalyst was 2.3% by weight.

Example 12

3 g sodium carbonate were dissolved in 20 ml distilled water (c=150 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The sodium content of the catalyst was 2.4% by weight.

Example 13

3 g rubidium carbonate were dissolved in 20 ml distilled water (c=150 g/l) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The rubidium content of the catalyst was 4.8% by weight.

Example 14

3 g cesium carbonate were dissolved in 20 ml distilled water (c=150 g/l alkali metal carbonate solution) and the 1.4 g wet (1 g dry) catalyst were suspended in the solution and stirred at room temperature for 1 hour. After modification the suspension was decanted and the catalyst was washed three times with 20 ml ethanol and twice with 20 ml cyclohexane. The cesium content of the catalyst was 5.9% by weight.

Example 15

30 g potassium carbonate were dissolved in 200 ml distilled water (c=150 g/l). 10 g dry nickel catalyst on $SiO_2$ (kieselguhr)/MgO (pulverulent Ni 55/5 TS from Celanese) were suspended in the solution and stirred at room temperature for 1 hour. After modification the suspension was decanted, the catalyst was washed five times with 20 ml ethanol and dried by vacuum. The potassium content of the catalyst was 3% by weight.

Example 16

30 g potassium carbonate were dissolved in 200 ml distilled water (c=150 g/l). 10 g dry nickel catalyst on kieselguhr/$Al_2O_3$ (pulverulent Ni 62/15 TS from Celanese) were suspended in the solution and stirred at room temperature for 1 hour. After modification the suspension was decanted, the catalyst was washed five times with 20 ml ethanol and dried by vacuum. The potassium content of the catalyst was 3.5% by weight.

Example 17

30 g potassium carbonate were dissolved in 200 ml distilled water (c=150 g/l). 10 g dry cobalt catalyst on kieselguhr (pulverulent Co 45/20 TS from Celanese) were suspended in the solution and stirred at room temperature for 1 hour. After modification the suspension was decanted, the catalyst was washed five times with 20 ml ethanol and dried by vacuum. The potassium content of the catalyst was 3.3% by weight.

Example 18

30 g potassium carbonate were dissolved in 200 ml distilled water (c=150 g/l). 14 g wet Raney cobalt catalyst B 2112 Z were suspended in the solution and stirred at room temperature for 1 hour. After modification the suspension was decanted and the catalyst pressure-filtered under nitrogen. The potassium content of the catalyst was 3% by weight.

TABLE 1

Modified catalysts

| Example | Modifier | Catalyst | Alkali metal content of the catalyst, % by wt. |
|---|---|---|---|
| 1 | Potassium carbonate | Raney nickel | 2.4 |
| 2 | Potassium carbonate | Raney nickel | 3.2 |
| 3 | Potassium carbonate | Raney nickel | 4.1 |
| 4 | Potassium carbonate | Raney nickel | 4.6 |
| 5 | Potassium carbonate | Raney nickel | 7.1 |
| 6 | Potassium carbonate | Raney nickel | 3.2 |
| 7 | Potassium carbonate | Raney nickel | 3.3 |
| 8 | Potassium carbonate | Raney nickel | 3.1 |
| 9 | Potassium carbonate | Raney nickel | 3.8 |
| 10 | Potassium carbonate | Raney nickel | 3.9 |
| 11 | Potassium hydrogencarbonate | Raney nickel | 2.3 |
| 12 | Sodium carbonate | Raney nickel | 2.4 |
| 13 | Rubidium carbonate | Raney nickel | 4.8 |
| 14 | Cesium carbonate | Raney nickel | 5.9 |
| 15 | Potassium carbonate | Nickel | 3 |
| 16 | Potassium carbonate | Nickel | 3.5 |
| 17 | Potassium carbonate | Cobalt | 3.3 |
| 18 | Potassium carbonate | Raney cobalt | 3 |

Hydrogenation of Nitrile

Control Example 19 (Not an Example of this Invention)

A 300 ml stainless steel reactor was charged with 100 ml (0.447 mol) lauronitrile, and 1.4 g wet unmodified Raney nickel catalyst. The reaction was run under 10 bar hydrogen pressure at 125° C. for 2 hours, and the reaction mixture was stirred at a rate of 1500 rpm. The yield of dodecylamine was 83.2% at a conversion of 99.7%.

Example 20 (Not an Example of this Invention)

The reactor was charged with 100 ml (0.447 mol) lauronitrile, 1.4 g wet unmodified Raney nickel catalyst, and 2.28 g (0.134 mol) ammonia. The reaction was run under 10 bar hydrogen pressure at 125° C. for 4 hours, and the reaction mixture was stirred at a rate of 1500 rpm. The yield of dodecylamine was 93.6% at a conversion of 99.8%.

Example 21

A reactor was charged with 100 ml lauronitrile, and 1.4 g wet Raney nickel catalyst modified with 150 g/l $K_2CO_3$ solution as given in Example 2. The reaction was run under 10 bar hydrogen pressure at 125° C. for 2 hours, and the reaction mixture was stirred at 1500 rpm. The yield of dodecylamine was 97.2% at a conversion of 99.8%.

Example 22

The reactor was charged with 100 ml lauronitrile, 1.4 g Raney nickel catalyst modified with 150 g/l $K_2CO_3$ solution (Example 2), and 2.28 g (0.134 mol) ammonia. The reaction was run under 10 bar hydrogen pressure at 125° C. for 2 hours, and the reaction mixture was stirred at a rate of 1500 rpm. The yield of dodecylamine was 99.4% at a conversion of 99.6%.

Example 23

The procedure of Example 21 was repeated except that the Raney nickel catalyst was modified with 100 g/l $K_2CO_3$ solution as given in Example 1. The yield of dodecylamine was 95.9% at 2 hours reaction time and a conversion of 99.9%.

Example 24

The procedure of Example 21 was repeated except that the Raney nickel catalyst was modified with 200 g/l $K_2CO_3$ solution as given in Example 3. The yield of dodecylamine was 91.0% at 2 hours reaction time and a conversion of 93.0%.

Example 25

The procedure of Example 21 was repeated except that the Raney nickel catalyst was modified with 400 g/l $K_2CO_3$ solution as given in Example 4. The yield of dodecylamine was 68.3% at 2 hours reaction time and a conversion of 69.9%.

Example 26

The procedure of Example 21 was repeated except that the Raney nickel catalyst was modified with 150 g/l $K_2CO_3$ solution as given in Example 5. The yield of dodecylamine was 60.5% at 4 hours reaction time and a conversion of 61.7%.

Example 27

The procedure of Example 21 was repeated except that the Raney nickel catalyst was modified with 150 g/l $K_2CO_3$ solution as given in Example 6. The yield of dodecylamine was 95.8% at 2 hours reaction time and a conversion of 99.8%.

Example 28

The procedure of Example 21 was repeated except that the Raney nickel catalyst was modified with 150 g/l $K_2CO_3$ solution as given in Example 7. The yield of dodecylamine was 96.1% at 2 hours reaction time and a conversion of 99.5%.

Example 29

The procedure of Example 21 was repeated except that the Raney nickel catalyst was modified with 150 g/l $K_2CO_3$ solution as given in Example 8. The yield of dodecylamine was 95.4% at 2 hours reaction time and a conversion of 99.9%.

Example 30

The procedure of Example 21 was repeated except that the Raney nickel catalyst was modified with 143 g/l $K_2CO_3$ solution as given in Example 9. The yield of dodecylamine was 92.3% at 2 hours reaction time and a conversion of 94.3%.

Example 31

A reactor was charged with 20 ml lauronitrile, 80 ml cyclohexane, and 1.4 g Raney nickel catalyst modified with 150 g/l $K_2CO_3$ solution. The reaction was run under 10 bar hydrogen pressure at 125° C., and the reaction mixture was stirred at 1500 rpm. The conversion of lauronitrile was 99.6% and the yield of dodecylamine was 95.0%.

Example 32

The procedure of Example 21 was repeated except that the Raney nickel catalyst was modified with 100 g/l $KHCO_3$ solution as given in Example 11. The yield of dodecylamine was 93.6% at 1 hour reaction time and a conversion of 99.4%.

Example 33

The procedure of Example 21 was repeated except that the Raney nickel catalyst was modified with 100 g/l $Na_2CO_3$ solution as given in Example 12. The yield of dodecylamine was 84.2% at 1 hour reaction time and a conversion of 98.9%.

Example 34

The procedure of Example 21 was repeated except that the Raney nickel catalyst was modified with 150 g/l $Rb_2CO_3$ solution as given in Example 13. The yield of dodecylamine was 96.3% at 2 hours reaction time and a conversion of 99.7%.

Example 35

The procedure of Example 21 was repeated except that the Raney nickel catalyst was modified with 150 g/l $Cs_2CO_3$ solution as given in Example 14. The yield of dodecylamine was 97.3% at 2 hours reaction time and a conversion of 99.2%.

Example 36

The reactor was charged with 100 ml lauronitrile, 1 g nickel catalyst, modified with 150 g/l $K_2CO_3$ solution, on kieselguhr/MgO (Example 15) and 2 g (0.12 mol) ammonia. The reaction was run under 15 bar hydrogen pressure at 125° C. for 3 hours, and the reaction mixture was stirred at 1500 rpm. The yield of dodecylamine was 99.2% at a conversion of 99.5%.

Example 37

The reactor was charged with 100 ml oleonitrile, 1 g nickel catalyst, modified with 150 g/l $K_2CO_3$ solution, on kieselguhr/$Al_2O_3$ (Example 16) and 2 g (0.12 mol) ammonia. The reaction was run under 10 bar hydrogen pressure at 120° C. for 2 hours, and the reaction mixture was stirred at 1500 rpm. The yield of primary amines (oleylamine) was 99.3% at a conversion of 99.7%.

Example 38

The reactor was charged with 100 ml oleonitrile, 1 g cobalt catalyst, modified with 150 g/l $K_2CO_3$ solution, on kieselguhr (Example 17) and 3 g (0.12 mol) ammonia. The reaction was run under 60 bar hydrogen pressure at 140° C. for 4 hours, and the reaction mixture was stirred at 1500 rpm. The yield of primary amines (oleylamine) was 99.6% at a conversion of 99.8%.

Example 39

The reactor was charged with 100 ml lauronitrile, 1 g Raney cobalt catalyst modified with 150 g/l $K_2CO_3$ solution (Example 18) and 2 g (0.12 mol) ammonia. The reaction was run under 50 bar hydrogen pressure at 160° C. for 4 hours, and the reaction mixture was stirred at 1500 rpm. The yield of dodecylamine was 98.8% at a conversion of 99.2%.

Examples 40 to 43

The activity on repeated use of Raney nickel catalyst in the hydrogenation of lauronitrile was investigated.

The autoclave (volume 10 l) was charged with 5 kg lauronitrile, 100 g Raney nickel catalyst and optionally 250 g ammonia. The reaction was carried out at 10 bar hydrogen, 125° C. and a stir rate of 1000 rpm. The lauronitrile conversion and the selectivity for dodecylamine were determined at different reaction times by amounts of catalyst falling as a result of recycling and sampling losses. Measurements were carried out using modified and unmodified catalyst. The catalyst was modified in accordance with Example 10.

TABLE 3

Hydrogenation of lauronitrile using unmodified catalyst and without addition of ammonia (Example 41)

| Catalyst use No. | Amount of catalyst g | Reaction time h | Conversion % | Selectivity % |
|---|---|---|---|---|
| 1 | 100 | 3.1 | 99.9 | 88.3 |
| 2 | 95 | 3.5 | 99.8 | 87.7 |
| 3 | 88 | 3.5 | 100 | 85.6 |
| 4 | 81 | 3.6 | 99.7 | 85.8 |
| 5 | 74 | 4.0 | 99.9 | 85.4 |

TABLE 4

Hydrogenation of lauronitrile with unmodified catalyst with addition of ammonia (Example 42)

| Catalyst use No. | Amount of catalyst g | Reaction time h | Conversion % | Selectivity % |
|---|---|---|---|---|
| 1 | 100 | 3.7 | 100 | 97.6 |
| 2 | 94 | 5.2 | 92.9 | 93.7 |
| 3 | 84 | 6.1 | 85.7 | 94.5 |
| 4 | 73 | 7.8 | 92.4 | 96.0 |
| 5 | 65 | 9.5 | 73.2 | 95.9 |

TABLE 2

Results of the hydrogenation

| Example | Catalyst | Ammonia | Conversion, % | Selectivity, % | Amine |
|---|---|---|---|---|---|
| 19 (C) | Raney nickel | no | 99.7 | 83.2 | Dodecylamine |
| 20 (C) | Raney nickel | yes | 99.8 | 93.6 | Dodecylamine |
| 21 | Raney nickel | no | 99.8 | 97.2 | Dodecylamine |
| 22 | Raney nickel | yes | 99.6 | 99.4 | Dodecylamine |
| 23 | Raney nickel | no | 99.9 | 95.9 | Dodecylamine |
| 24 | Raney nickel | no | 93.0 | 91.0 | Dodecylamine |
| 25 | Raney nickel | no | 69.9 | 68.3 | Dodecylamine |
| 26 | Raney nickel | no | 61.7 | 60.5 | Dodecylamine |
| 27 | Raney nickel | no | 99.8 | 95.8 | Dodecylamine |
| 28 | Raney nickel | no | 99.5 | 96.1 | Dodecylamine |
| 29 | Raney nickel | no | 99.9 | 95.4 | Dodecylamine |
| 30 | Raney nickel | no | 94.3 | 92.3 | Dodecylamine |
| 31 | Raney nickel | no | 99.6 | 95.0 | Dodecylamine |
| 32 | Raney nickel | no | 99.4 | 93.6 | Dodecylamine |
| 33 | Raney nickel | no | 98.9 | 84.2 | Dodecylamine |
| 34 | Raney nickel | no | 99.7 | 96.3 | Dodecylamine |
| 35 | Raney nickel | no | 99.2 | 97.3 | Dodecylamine |
| 36 | Nickel | yes | 99.5 | 99.2 | Dodecylamine |
| 37 | Nickel | yes | 99.7 | 99.3 | Oleylamine |
| 38 | Cobalt | yes | 99.8 | 99.6 | Oleylamine |
| 39 | Raney cobalt | yes | 99.2 | 98.8 | Dodecylamine |

TABLE 5

Hydrogenation of lauronitrile with modified catalyst without addition of ammonia (Example 43)

| Catalyst use No. | Amount of catalyst g | Reaction time h | Conversion % | Selectivity % |
|---|---|---|---|---|
| 1 | 100 | 3.6 | 100 | 98.1 |
| 2 | 94 | 5.8 | 99.9 | 93.0 |
| 3 | 85 | 7.4 | 100 | 94.6 |
| 4 | 77 | 12.3 | 99.8 | 95.7 |
| 5 | 69 | 23.6 | 99.7 | 95.9 |

TABLE 6

Hydrogenation of lauronitrile with modified catalyst and with addition of ammonia (Example 44)

| Catalyst use No. | Amount of catalyst g | Reaction time h | Conversion % | Selectivity % |
|---|---|---|---|---|
| 1 | 100 | 3.5 | 99.6 | 99.9 |
| 2 | 94 | 8.1 | 99.2 | 99.9 |
| 3 | 88 | 10.6 | 99.1 | 99.7 |
| 4 | 79 | 11.8 | 99.5 | 98.7 |
| 5 | 70 | 10.3 | 100 | 99.4 |

The invention claimed is:

1. A process for preparing a primary amine, said process comprising hydrogenating a reaction mixture which comprises
   (a) at least one nitrile,
   (b) hydrogen, and
   (c) a modified catalyst comprising at least one cobalt or nickel catalyst which contains alkali metal carbonate or hydrogencarbonate in an amount of from 2 to 12% by weight wherein said modified catalyst is modified ex situ by adsorption of an alkali metal carbonate or alkali metal hydrogencarbonate.

2. The process as claimed in claim 1, in which the modified catalyst is prepared using alkali metal carbonates or alkali metal hydrogencarbonates by adsorption from an aqueous solution having a concentration of from 10 g/l to 400 g/l.

3. The process as claimed in claim 2, in which the aqueous solution comprises $K_2CO_3$ having a concentration in the range from 50 to 200 g/l.

4. The process of claim 1, wherein the modified catalyst is a modified Raney nickel catalyst.

5. The process of claim 1, wherein the nitrile is of the formula R—CN in which R is a hydrocarbon group having from 1 to 32 carbon atoms.

6. The process of claim 1, in which the modified catalyst is present in the reaction mixture in an amount of from 1 to 10% by weight based on the nitrile.

7. The process of claim 1, in which said process is carried out in the presence of ammonia in an amount of from 1 to 10% by weight based on the nitrile.

8. The process of claim 1, in which said process is carried out in the presence of cyclohexane.

9. The process of claim 1, in which said process is carried out under a hydrogen pressure of from 1 to 200 bar.

10. The process of claim 1, in which said process is carried out in the temperature range of from 60 to 250° C.

11. The process of claim 1, in which said process is carried out under a hydrogen pressure of from 2 to 30 bar.

12. The process of claim 1, in which said process is carried out in the temperature range of from 100 to 150° C.

13. The process of claim 1, wherein the reaction mixture further comprises ammonia.

* * * * *